US008715701B2

(12) United States Patent
Lipkowski et al.

(10) Patent No.: US 8,715,701 B2
(45) Date of Patent: May 6, 2014

(54) MICROSTRUCTURAL PROTEIN PREPARATIONS CONTAINING ADSORBED BIOLOGICALLY ACTIVE SUBSTANCES AND THEIR APPLICATION IN MEDICINE AND COSMETICS

(75) Inventors: Andrzej Lipkowski, Warsaw (PL); Anna Grabowska, Warsaw (PL); Katarzyna Kurzepa, Warka (PL); Aleksandra Szczucinska, Warsaw (PL)

(73) Assignee: Instytut Medycyny Doswiadczalnej I Klinicznej, Warsaw (PL)

( * ) Notice: Subject to any disclaimer, the term of this patent is extended or adjusted under 35 U.S.C. 154(b) by 934 days.

(21) Appl. No.: 12/312,576

(22) PCT Filed: Nov. 20, 2007

(86) PCT No.: PCT/PL2007/000078
§ 371 (c)(1),
(2), (4) Date: Jul. 24, 2009

(87) PCT Pub. No.: WO2008/063092
PCT Pub. Date: May 29, 2008

(65) Prior Publication Data
US 2010/0047196 A1 Feb. 25, 2010

(30) Foreign Application Priority Data
Nov. 21, 2006 (PL) .......................... 381103

(51) Int. Cl.
*A61K 8/02* (2006.01)
*A61K 8/49* (2006.01)
*A61K 9/70* (2006.01)
*A61K 9/14* (2006.01)
*A61K 31/715* (2006.01)
*A61K 31/19* (2006.01)
*A01N 25/34* (2006.01)
*A61Q 17/04* (2006.01)
*A61F 13/00* (2006.01)
*A61L 15/16* (2006.01)
*A01N 43/04* (2006.01)
*A01N 37/36* (2006.01)
*A61P 21/02* (2006.01)

(52) U.S. Cl.
USPC ........... 424/401; 424/59; 424/70.1; 424/70.9; 424/74; 424/402; 424/404; 424/422; 424/423; 424/425; 424/443; 424/445; 424/447; 424/484; 424/489; 424/725; 424/780; 514/2; 514/12; 514/59; 514/159; 514/282; 514/329; 514/567; 514/570; 514/630; 514/773; 530/357

(58) Field of Classification Search
USPC ......... 424/401, 402, 404, 422, 423, 425, 443, 424/445, 447, 484, 489, 59, 70.1, 70.9, 74, 424/725, 780; 530/357; 514/2, 12, 59, 159, 514/282, 329, 567, 570, 630, 773
See application file for complete search history.

(56) References Cited

U.S. PATENT DOCUMENTS

| 2,854,381 | A | 9/1958 | Kuna |
| 6,544,548 | B1 | 4/2003 | Siller-Jackson et al. |
| 2005/0058686 | A1* | 3/2005 | Van Dyke et al. ............ 424/426 |
| 2005/0232875 | A1* | 10/2005 | Umeda et al. .................. 424/59 |

FOREIGN PATENT DOCUMENTS

| EP | 1815843 | 8/2007 | |
| EP | 1878423 | 1/2008 | |
| WO | 03064449 | 8/2003 | |
| WO | WO03/064449 A2 * | 8/2003 | ........... C07K 14/435 |
| WO | 2004047774 | 6/2004 | |
| WO | 2007050387 | 5/2007 | |
| WO | WO2007/050387 A2 * | 5/2007 | ............... A61K 9/14 |

OTHER PUBLICATIONS

Tanabe et al., "Fabrication of cell scaffolds for tissue engineering from wool keratin," 2007; Materials Integration; 20(11): 107-112; Abstract only. https://scifinder.cas.org/scifinder/view/scifinder/scifinderExplore.jsf.*
Seacoast Vitamins Online Catalog; http://www.seacoast.com/topic.php?health=keratin+reservatrol (downloaded Sep. 28, 2011).*
ApHogee "Healthy Hair Beauty Supply" 2008 review; http://www.blackhaircare101.com/ApHogee_Keratin_and_Green_Tea_Restructurizer_Review_Guide (downloaded Sep. 28, 2011).*
Herbs and Botanicals: Antelope's Horn (ling yang jiao). Acupuncture Today [online], [retrieved on Jun. 6, 2012]. Retrieved from the Internet <URL: http://www.acupuncturetoday.com/herbcentral/antelopes_horn.php>.*
How to Prepare Your Own Decoction. House of Yang (BVI) Limited [online], [retrieved on Jun. 6, 2012]. Retrieved from the Internet <URL: http://www.houseofyinyang.com/eng/hoyy/decoction/main.htm>.*
Herbs and Botanicals: Antelope's Horn (ling yang jiao). Acupuncture Today [online], [retrieved on Ju. 6, 2012]. Retrieved from the Internet <URL: http://www.acupuncturetoday.com/herbcentral/antelopes_horn.php>.*
How to Prepare Your Own Decoction. House of Yang (BVI) Limited [online], [retrieved on Jun. 6, 2012]. Retrieved from the Internet <URL: http://houseofyinyang.com/eng/hoyy/decoction/main.htm.*
Tanabe et al., "Fabrication of cell scaffolds for tissue engineering from wool keratin," 2007; Materials Integration; 20(00): 107-112; Abstract only—previously supplied.*

(Continued)

*Primary Examiner* — Jane C Oswecki
(74) *Attorney, Agent, or Firm* — Gary J. Gershik; Cooper & Dunham LLP

(57) ABSTRACT

Protein preparations containing biologically active compounds and the application of the protein preparations obtained, particularly as a component of medicinal and cosmetic preparations as protective substances or in the regeneration of cells and tissues of the human organism, and which can comprise a component of culture media for dermal or hepatic tissues, or for stem cells destined for use in the regeneration of cells and tissues in the human organism.

7 Claims, No Drawings

(56) References Cited

OTHER PUBLICATIONS

Herbs and Botanicals: Antelope's Horn (ling yang jiao). Acupuncture Today [online], [retrieved on Jun. 6, 2012]. Retrieved from the Internet<URL:http://www.acupuncturetoday.com/hercentral/antelopes_horn.php> Previously supplied.*

Tanabe et al., "Fabrication of cell scaffolds for tissue engineering from wool keratin," 2007; Materials Integration; 20(00):107-112; Abstract only—previously supplied.*

ApHogee "Healthy Hair Beauty Supply", 2008 review; http://www.blackhaircare101.com/ApHogee_Keratin_and_Green_Tea_Restructurizer_Review_Guide (downloaded from the Internet Sep. 28, 2011)—previously supplied.*

Herbs and Botanicals: Antelope's Horn (ling yang jiao). Acupuncture Today [online], [retrieved on Jun. 6, 2012]. Retrieved from the Internet<URL: http://www.acupuncturetoday.com/herbcentral/antelopes_horn.php> Previously supplied.*

How to Prepare Your Own Decoction. House of Yang (BVI) Limited [online], [retrieved on Jun. 6, 2012]. Retrieved from the Internet<URL: http://houseofyinyang.com/eng/hoyy/decoction/main.htm. Previously supplied.*

Seacoast Vitamins Online Catalog; http://www.seacoast.com/topic.php?health=keratin+reservatrol (downloaded Sep. 28, 2011). Previously provided.*

Database CA Chemical Abstract Service, Columbus, Ohio, US; XP002518855, retrieved from STN database accession No. 131:74917, (1999).

Database CA Chemical Abstract Service, Columbus, Ohio, US; XP002518856, retrieved from STN database accession No. 136:221771, (2002).

Database CA Chemical Abstract Service, Columbus, Ohio, US; XP002518854, retrieved from STN database accession No. 144:288969.

F. Merki et al., "Beziehungen zwischen den physikalisch-chemischen Eigenschaften, der chemischen Reaktivitat under lokalanasthetischen Wirkung 32. Mitteilung (1. Teil)" Arzneimittel-Forschung, vol. 25, No. 7, 1975, pp. 997-1004, XP008103664.

F. Merki et al., "Beziehungen zwischen den physikalisch-chemischen Eigenschaften, der chemischen Reaktivitat under lokalanasthetischen Wirkung 32. Mitteilung (2. Teil)" Arzneimittel-Forschung, vol. 25, No. 8, 1975, pp. 1233-1240, XP008103667.

International Search Report issued by the International Searching Authority (ISA/EP) on Mar. 23, 2009 in connection with International Application No. PCT/PL2007/000078.

Written Opinion of the PCT/PL2007/000078, dated May 21, 2009.

International Preliminary Report on Patentability for PCT/PL2007/000078, dated May 26, 2009.

Lipkowski et al. (2009) "Keratin-associated Protein Micromaterials for Medical and Cosmetic Applications." Polimery, 54 (5) : 386-388.

\* cited by examiner

MICROSTRUCTURAL PROTEIN PREPARATIONS CONTAINING ADSORBED BIOLOGICALLY ACTIVE SUBSTANCES AND THEIR APPLICATION IN MEDICINE AND COSMETICS

This application is a §371 National Stage of PCT International Application No. PCT/PL2007/000078, filed Nov. 20, 2007, claiming priority of Polish Application No. P-381103 filed Nov. 21, 2006 the contents of which are hereby incorporated by reference into this application.

The subject of the present invention are novel microstructural protein preparations containing adsorbed biologically active substances and their application in medicine and cosmetics.

The traditional administration of an active substance in medicine or cosmetics, such as intramuscular or intravenous, or as oral capsules or as lotions or creams containing the active substance are generally characterized by a rapid but short-lived increase of the concentration of the active substance. Conglomerates of the active substance and a high-molecular mass substance are used to prolong its release period. Such compounds release the active substance by way of diffusion and/or degradation of the high molecular mass compound.

Bożenna Baranowska, Andrzej Lipkowski, Ewa Marczak, Irmina Makulec, Hanna Rybak, Joanna Pastuszak, Anna Szulc, Aleksandra Szczucińska, Wiesława Wasilewicz-Niedbalska, and Zofia Grabska have patented "*A method of obtaining an abrasive agent for cleaning and exfoliating skin*", Polish Patent PL 179302, for obtaining protein preparations for use as an exfoliant in cosmetics. The method of obtaining the preparation according to said patent description consisted of the enzymatic digestion of natural structural protein sources, including hair, bristles, wool or feathers and then grinding the remaining solids to a protein preparation of predetermined particle size. Research showed that cosmetics containing protein preparations according to said patent were not allergenic when used as an exfoliant in cream. A modification of the manufacturing process was proposed as a result of further research which consisted of repeated enzymatic digestion of the source material. This process was described in the Polish patent application by Andrzej W. Lipkowski, Marcin Jurga, Krystyna Domańska-Janik, Barbara Łukomska, entitled "New protein skeleton preparations, their production and applications", P380011 and leads to the production of a protein preparation, which may be applied in animals, humans and in stem cell cultures. Further structural research of the material produced showed that it has a microporous structure. The goal of the present invention is to propose the production of new protein preparations, where active substances are adsorbed onto the highly developed surface and into micropores, which facilitate the application of said preparations as the active substance in medicinal compounds or cosmetics.

Unexpectedly, this goal has been realized in the present invention.

Unexpectedly, it has been shown that biologically active substances such as high-molecular mass proteins and peptides or lipophylic low-molecular mass compounds effectively adsorb onto the highly developed surfaces and micropores of protein preparations. These new microstructural protein preparations can constitute the active component in medicinal or cosmetic preparations with active substances adsorbed onto them. Following application, the active substance is slowly released from the protein preparation. Due to this, one obtains the complementary activity of the protein preparation as a skeletal structural material and long-term active substance activity which acts at the application site. As a result, new protein preparations with adsorbed active substances can be used in medicine and cosmetics, particularly in such cases as wound treatment, skin protection, post-surgical lesion repair, and in vitro cell and tissue cultures.

To better illustrate the present invention, novel scaffolding protein preparations and the method of obtaining novel scaffolding protein preparations, and the application of said preparations in stem cell cultures. The scope of the present invention should not be limited to the contents of the examples below.

EXAMPLE I 1 kg of sheep's wool was placed in 1% lye and mixed for 1 hour at room temperature. The lye was then drained off and the wool was washed twice in water and suspended in water. The suspension was acidified with hydrochloric acid to pH 2.2 and pepsin was added. The mixture was agitated for 3 hours at 35° C., and then the wool solids were drained off, washed twice in water and sieved to collect particles of less than 1 mm in length. The preparation produced was inundated with 1% lye and then drained after 1 h, washed in water and then in 1% hydrochloric acid and drained. The remainder was suspended in water, acidified to pH 2.2 and pepsin was added. The suspension was mixed for 2 h at 35° C., then drained, washed three times in water and dried. 500 g of scaffolding protein material from sheep's wool was obtained, and was designated SSP-2.

100 g of Dry SSP-2 was placed in 1000 ml of Merlot wine. The suspension of SSP-2 in wine was mixed for 20 minutes at 30° C. and then drained off. The precipitate was washed three times under water. After drying, 105 g of SSP-2 with adsorbed wine polyphenols were obtained. Following drying, the preparation was added to regenerating skin cream.

EXAMPLE II 50 g of dry SSP-2 obtained as in Example I was supplemented with 100 ml ethyl acetate extract from green tea. The SSP-2 suspension was mixed intensively for 20 minutes at 30° C., and then drained, and the filtrate was washed twice in ethanol. Following drying, 55 g of SSP-2 with suspended green tea polyphenols were obtained. After drying, the preparation was added to a skin regenerating cream.

EXAMPLE III 5 g of dry SSP-2 obtained as in Example I were supplemented with 20 ml of a 20% colchicine solution in 10% ethanol. The SSP-2 suspension was mixed intensively for 20 minutes at 30° C., drained, and the filtrate was washed twice in water. After drying, 55 g of SSP-2 were obtained for use in creams for treating inflammation.

EXAMPLE IV 100 g of human hair were inundated with 1% lye and mixed for 1 hour at RT. The lye was drained off and the hair was washed twice in water and suspended in water. The suspension was acidified with HCl to pH 2.2 and pepsin was added. The mixture was agitated for 3 hours at 35° C., and then the hair solids were drained off, washed twice in water and dried. The dry preparation was ground and sieved, collecting product smaller than 1 mm in length. The preparation obtained was suspended in 1% lye, and then centrifuged after 1 h, washed in 1% HCl and recentrifuged. The remainder was suspended in water, the suspension was acidified to pH 2.2 and pepsin was added. The suspension was mixed for 2 hours at 35° C., drained, washed thrice in water and dried. The dry preparation was ground again and sieved, collecting product less than 0.25 mm long. The preparation obtained was suspended in 1% lye, and then centrifuged after 1 h, washed in water, recentrifuged, washed in 1% HCl and centrifuged again. The remainder was suspended in water, the suspension was acidified to 2.2 and pepsin was added. The suspension was mixed for 2 h at 35° C., centrifuged and the insoluble portion was washed by suspending it in water, and then dried. 25 g of scaffolding protein material was obtained from human hair, designated as HSP-2.

0.5 g of dry and sterile HSP-2 were supplemented with 2 mg of fibronectin from human serum suspended in 2 ml of sterile water. The aqueous solution completely adsorbed onto HSP-2. The product was washed in 50% ethanol and dried in a desiccators under reduced pressure. After drying, the product was used as a component of a medium used for in a culturing human skin tissue.

EXAMPLE V 5 g of dry HSP-2 obtained as in Example IV, were supplemented under sterile conditions with 10 ml of an aqueous solution of the opioid peptide morphoceptin and the antibiotic penicillin. After the solution was absorbed, the preparation was dired. The product was used as a wound powder for difficult-to-heal diabetic lesions. Wound closure and healing were observed.

The invention claimed is:

1. A composition comprising a scaffolding protein preparation obtained from products of vertebrate animal epithelia from which soluble proteins and pepsin-digestible fragments are removed, and a biologically active compound adsorbed on to the scaffolding protein preparation, wherein the vertebrate animal epithelia is sheep's wool, human hair, bristles or feathers, and wherein the biologically active compound is red wine extract, green tea polyphenols, colchicines, fibronectin, morphoceptin or penicillin.

2. The composition of claim 1, wherein the biologically active compound is a component for treating skin wounds or skin inflammation or skin bacteria or skin infections.

3. The composition of claim 1, formulated as a subdermal implant.

4. The composition of claim 1, wherein the animal is a bird.

5. The composition of claim 1, wherein the animal is a mammal.

6. The composition of claim 1, wherein the biologically active compound is adsorbed on to the scaffolding protein preparation by mixing the scaffolding protein preparation with an aqueous solution of the biologically active compound and then drying.

7. The composition of claim 1, wherein the biologically active compound is adsorbed on to the scaffolding protein preparation by mixing the scaffolding protein preparation with a polar organic solution of the biologically active compound and then drying.

* * * * *

UNITED STATES PATENT AND TRADEMARK OFFICE
CERTIFICATE OF CORRECTION

PATENT NO. : 8,715,701 B2  
APPLICATION NO. : 12/312576  
DATED : May 6, 2014  
INVENTOR(S) : Lipkowski et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

Signed and Sealed this

Twenty-ninth Day of September, 2015

Michelle K. Lee
*Director of the United States Patent and Trademark Office*